US011676702B2

(12) United States Patent
Barkan et al.

(10) Patent No.: US 11,676,702 B2
(45) Date of Patent: Jun. 13, 2023

(54) METHOD FOR AUTOMATIC VISUAL ANNOTATION OF RADIOLOGICAL IMAGES FROM PATIENT CLINICAL DATA

(71) Applicant: International Business Machines Corporation, Armonk, NY (US)

(72) Inventors: Ella Barkan, Haifa (IL); Pavel Kisilev, Maalot (IL); Eugene Walach, Haifa (IL)

(73) Assignee: International Business Machines Corporation, Armonk, NY (US)

( * ) Notice: Subject to any disclaimer, the term of this patent is extended or adjusted under 35 U.S.C. 154(b) by 131 days.

(21) Appl. No.: 16/714,834

(22) Filed: Dec. 16, 2019

(65) Prior Publication Data

US 2021/0183499 A1  Jun. 17, 2021

(51) Int. Cl.
*G06F 17/00* (2019.01)
*G16H 30/40* (2018.01)
*G06F 40/30* (2020.01)
*G06F 40/169* (2020.01)
*G16H 30/20* (2018.01)

(52) U.S. Cl.
CPC ........... *G16H 30/40* (2018.01); *G06F 40/169* (2020.01); *G06F 40/30* (2020.01); *G16H 30/20* (2018.01)

(58) Field of Classification Search
CPC ........ G06F 30/40; G06F 40/169; G06F 40/30; G16H 30/40; G06H 30/20
USPC .................. 715/230, 203; 382/128, 177, 190
See application file for complete search history.

(56) References Cited

U.S. PATENT DOCUMENTS

| 8,218,849 | B2* | 7/2012 | Lu | G06V 10/768 |
| | | | | 382/131 |
| 8,311,303 | B2* | 11/2012 | Suehling | G16H 30/40 |
| | | | | 382/128 |
| 9,355,105 | B2* | 5/2016 | Wang | G06F 16/13 |
| 10,140,273 | B2* | 11/2018 | Biegert | G06F 40/30 |
| 10,593,423 | B2* | 3/2020 | Baldwin | G06F 16/3329 |
| 10,729,396 | B2* | 8/2020 | Reicher | A61B 5/743 |

(Continued)

OTHER PUBLICATIONS

Riadh Bouslimi et al., "Using a Bag of Words for Automatic Medical Image Annotation With a Latent Semantic", International Journal of Artificial Intelligence & Applications (IJAIA), vol. 4, No. 3, May 2013.

(Continued)

*Primary Examiner* — Wilson W Tsui
*Assistant Examiner* — Matthew J Ludwig
(74) *Attorney, Agent, or Firm* — Gregory J Kirsch

(57) ABSTRACT

Presented herein are methods, systems, devices, and computer-readable media for image annotation for medical procedures. The system operates in a parallel manner. In one flow, the system starts from clinical terms and image and applies image detection module in order to get visual candidates for related radiological finding and provide them with semantic descriptors. In the second (parallel) flow, the system produces a list of prioritized semantic descriptors (with probabilities). The second flow is done by application of a reverse inference algorithm that uses clinical terms and expert clinical knowledge. The results of both flows combined by matching module for detection the best candidate and with limited user input images can be annotated. The clinical terms are extracted from clinical documents by textual analysis.

7 Claims, 5 Drawing Sheets

(56) References Cited

U.S. PATENT DOCUMENTS

| | | | | |
|---|---|---|---|---|
| 10,755,411 | B2* | 8/2020 | Zhang | G06T 7/0012 |
| 10,762,168 | B2* | 9/2020 | Qian | G16H 50/70 |
| 10,777,307 | B2* | 9/2020 | Schulze | G06F 3/0484 |
| 10,901,978 | B2* | 1/2021 | Xu | G16H 40/20 |
| 10,902,940 | B2* | 1/2021 | Lyman | G06F 21/6254 |
| 10,930,379 | B2* | 2/2021 | Sevenster | G16H 15/00 |
| 11,010,630 | B2* | 5/2021 | Yang | G06V 10/34 |
| 11,132,507 | B2* | 9/2021 | Park | G06N 3/0445 |
| 11,172,889 | B2* | 11/2021 | Park | A61B 8/085 |
| 2003/0105638 | A1* | 6/2003 | Taira | G10L 15/005 |
| | | | | 704/275 |
| 2010/0080434 | A1* | 4/2010 | Seifert | G06T 7/11 |
| | | | | 382/131 |
| 2011/0002520 | A1* | 1/2011 | Suehling | G06T 7/0012 |
| | | | | 382/154 |
| 2013/0066903 | A1* | 3/2013 | Tymoshenko | G06F 40/30 |
| | | | | 707/769 |
| 2014/0149407 | A1* | 5/2014 | Qian | G06F 16/35 |
| | | | | 707/758 |
| 2015/0332111 | A1* | 11/2015 | Kisilev | G06T 7/0012 |
| | | | | 382/131 |
| 2016/0217262 | A1* | 7/2016 | Sharbell | G06N 20/00 |
| 2018/0068076 | A1* | 3/2018 | Farri | G16H 70/60 |
| 2018/0108124 | A1* | 4/2018 | Guo | G06V 30/19173 |
| 2018/0239868 | A1* | 8/2018 | Kopylov | G16H 30/20 |
| 2018/0247405 | A1* | 8/2018 | Kisilev | G06T 7/0012 |
| 2019/0180153 | A1* | 6/2019 | Buckler | G06F 18/29 |
| 2019/0213484 | A1* | 7/2019 | Winn | G06F 16/334 |
| 2020/0401938 | A1* | 12/2020 | Etkin | G06V 10/768 |

OTHER PUBLICATIONS

Sascha Seiferta et al., "Semantic Annotation of Medical Images", Conference Paper in Proceedings of SPIE—The International Society for Optical Engineering—Mar. 2010.

* cited by examiner

US 11,676,702 B2

METHOD FOR AUTOMATIC VISUAL ANNOTATION OF RADIOLOGICAL IMAGES FROM PATIENT CLINICAL DATA

CROSS-REFERENCE TO RELATED APPLICATIONS

This application is a divisional of U.S. application Ser. No. 15/249,415, filed Aug. 28, 2016, the contents of which are hereby incorporated herein by reference.

FIELD OF TECHNOLOGY

The present invention relates to the technical field of medical image annotation. More particularly, the present invention is in the field of automated image annotation using reverse inference.

BACKGROUND OF THE INVENTION

Medical imaging has grown over the past decades to become an essential component of diagnoses and treatment. This field has seen significant developments in applications for computer-assisted diagnostics and image-guided medical procedures. These advances are tied, in part, to technical and scientific improvements in imaging. For example, some of the early work in this field in the late 1980s provided for medical image shape detection. These were some of the building blocks of systems developed in the mid-1990s and thereafter, such as image-guided surgery systems. These diagnostics systems aid medical practitioners in identifying diseases, and image-guided surgery makes use of imaging to aid a surgeon in performing more effective and accurate surgeries. These tools have become indispensable for diagnosis and therapy.

Furthermore, due to the rapid development of modern medical devices and the use of digital systems, more and more medical images are being generated. These images represent a valuable source of knowledge and are of significant importance for medical information retrieval. A single radiology department may produce tens of terabytes of data annually. Unfortunately, the sheer amount of medical visual data available makes it very difficult for users to find exactly the images that they are searching for. The development of Internet technologies has made medical images available in large numbers in online repositories, collections, atlases, and other health-related resources. This volume of digital medical imagery has led to an increase in the demand for automatic methods to index, compare, and analyze images. The ever-increasing amount of digitally produced images requires efficient methods to archive and access this data. Thus, the application of general image classification and retrieval techniques to this specialized domain has obtained increasing interest.

Among the challenges in image classification and retrieval is the difficulty in associating semantics to a medical image that has, in some cases, several pathologies. One option for assigning semantics to an image is annotation. Medical image annotation is the task of assigning to each image a keyword or a list of keywords that describe its semantic content. Annotations can be seen as a way of creating a correspondence between the visual aspects of multimedia data and their low-level features.

Several challenges remain for creating convenient tools for medical image annotation. One challenge for image annotation is in the semantics association process. There are generally three modalities of image annotation: manual, semiautomatic and automatic. The first type of annotation is done by a human giving each image a set of keywords. This image annotation process is a repetitive, difficult, and extremely time-consuming task. As such, it can benefit from automation.

The automatic annotation modality is a performed by a computer and aims to reduce the burden on the user. Automatic annotation has been driven by the goal of enhancing the annotation process and reducing ambiguity caused by repetitive annotations. However, there are several issues that arise in automating medical image annotations, including intra-class variability versus inter-class similarity and data imbalance. The first problem is due to the fact that images belonging to the same visual class might look very different, while images that belong to different visual classes might look very similar. In contrast to manual annotation, automatic annotation may decrease the precision of the output but increase overall productivity.

As a compromise between these two modalities, a combined approach has become necessary. This approach is known as the semi-automatic annotation. By incorporating user feedback, it is hoped that overall performance can be increased.

Across the varying modalities, current systems do not provide adequate mechanisms to annotate images. One or more of these problems and others are addressed by the systems, methods, devices, computer-readable media, techniques, and embodiments described herein. That is, some of the embodiments described herein may address one or more issues, while other embodiments may address different issues.

SUMMARY OF INVENTION

The present invention relates to a method for automatic visual annotation of large medical databases. Annotation of these databases provides a resource challenge, as the number of images and the computational load from annotating them is substantial. The present invention further relates to streamlining and automation of the annotation process.

The present invention, in an aspect provides a match between visual candidates and semantic descriptions extracted from patient case. The system may provide automatic extraction of both visual and semantic descriptions from the patient data.

The present invention, in another aspect, uses reverse inference for extracting semantic descriptions based on combining patient case data and expert clinical knowledge. The present invention, in a further aspect, operates based on generating and finding the most probable combination of clinical and image data representations for a given patient or case.

The present invention relates to a system that chooses the best candidate or candidates from the list of automatically located visual annotations on the image based on clinical case information. The system may include interfaces for the radiologist or other medical practitioner to approve the annotation. The radiologist or other medical practitioner's feedback can be used to improve the performance of the system by machine learning.

In embodiments, systems for medical image annotation comprise a standard medical vocabularies database, textual analysis engine operatively connected to the standard medical vocabularies database and configured to receive a set of textual data and generate a textual analysis result, an expert knowledge database, and a reverse inference engine operatively connected to the expert knowledge database and configured to receive the textual analysis result and generate a set of semantic descriptors.

In further embodiments, a method for medical image annotation comprises receiving a set of extracted clinical terms, wherein the set of extracted clinical terms are generated from an electronic patient case data file, receiving a set of expert knowledge from a database, performing reverse inference on the set of extracted clinical terms by applying the set of expert knowledge to produce a prioritized list of semantic descriptions, and determining the location of a radiological finding in an image by applying computer vision using the prioritized list of semantic descriptions.

The system, in an optional embodiment, may further comprise an object matching engine configured to receive an image and the output of the textual analysis engine and generate a set of semantic descriptions for visual candidates and a matching engine configured to match the set of semantic descriptors to the semantic descriptions for visual candidates. This embodiment helps to address the resource challenge, by streamlining and automating the annotation process, especially on large datasets.

The system may permissively comprise an interface for verification of the output of the matching engine. The set of semantic descriptions for visual candidates can comprises shape, density, and margins in optional embodiments. The object matching engine can use a computer vision algorithm in a permissive embodiment. The object matching engine can further use a machine learning algorithm in a permissive embodiment. The expert knowledge database may comprise a list of scored pairs of symptom to diagnosis, according to an optional embodiment. The expert knowledge database may also comprise scored lists of diseases and managements in a permissive embodiment. The expert knowledge database may further comprise the probability that a clinical clue is related to specific disease in an advantageous embodiment. The expert knowledge database can comprise the probability that semantic descriptions of radiological findings are related to a specific disease in a further advantageous embodiment.

Numerous other embodiments are described throughout herein. All of these embodiments are intended to be within the scope of the invention herein disclosed. Although various embodiments are described herein, it is to be understood that not necessarily all objects, advantages, features or concepts need to be achieved in accordance with any particular embodiment. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

The methods and systems disclosed herein may be implemented in any means for achieving various aspects, and may be executed in a form of a machine-readable medium embodying a set of instructions that, when executed by a machine, cause the machine to perform any of the operations disclosed herein. These and other features, aspects, and advantages of the present invention will become readily apparent to those skilled in the art and understood with reference to the following description, appended claims, and accompanying figures, the invention not being limited to any particular disclosed embodiment or embodiments.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and the invention may admit to other equally effective embodiments.

Other features of the present embodiments will be apparent from the Detailed Description that follows.

DETAILED DESCRIPTION OF THE EMBODIMENTS

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention. The following detailed description is therefore not to be taken in a limiting sense, and the scope of the present disclosure is defined by the appended claims and their equivalents.

Figure 1:
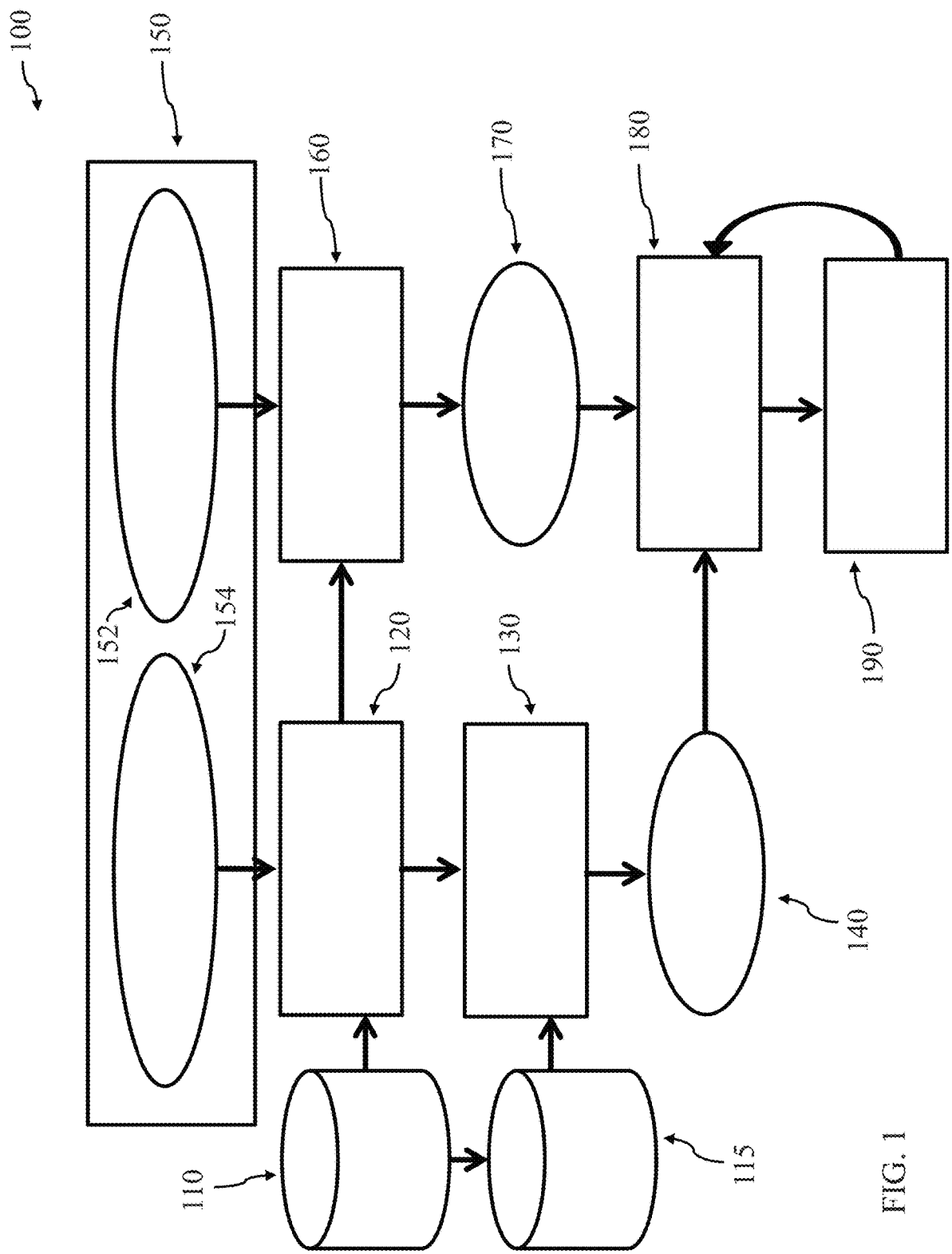
FIG. 1 illustrates a flow diagram of the various components and data sources, according to an embodiment of the present invention.

FIG. 1 illustrates a flow diagram 100 of the various components and data sources, according to an embodiment of the present invention. The system initially receives a patient case 150. The patient case can be received over a computer network interface or other data interface and can comprise an electronic data file or stream. This patient case 150 contains both a set of textual data 154 and a set of image data 152.

The set of image data 152 from the patient case can be of several different types. The image may be associated with a medical device, such as an ultrasound transducer. The image data 152 may be an ultrasound image, or the image may be a slice or image from other visualizable medical data, such as x-ray based methods, including conventional x-ray, computed tomography (CT), and mammography, molecular imaging and nuclear medicine techniques, magnetic resonance imaging, photography, endoscopy, elastography, tactile imaging, thermography, positron emission tomography (PET), and single-photon emission computed tomography (SPECT). The image data 152 includes modalities and studies.

The textual data 154 includes reports, physical examination, anamnesis, and diagnoses such as final diagnoses. The textual data 154 is fed into the textual analysis engine 120. The textual analysis engine 120 extracts the clinical terms. This is done by matching the textual content from the textual data 154 with terms in a standard medical vocabularies database 110. The match between text and vocabularies database 110 can be performed using natural language processing (NLP) and/or machine learning algorithms. The output of the textual analysis engine 120 includes the radiological finding type and a set of clinical terms. The radiological finding type is sent to the visual object matching engine 160.

The visual object matching engine 160 receives the radiological finding type, such as space occupying lesion (SOL), calcification, etc., along with the image data 152 from the patient case 150. The visual object matching engine 160 determines the location and semantic descriptors of all candidates for the radiological finding type extracted by the textual analysis engine 120. For example, the algorithm will return a list of visual candidates for SOL, where each candidate will have a semantic description such as shape, density, margins, etc. If the textual analysis engine 120 locates several findings, the same process (130, 140, 160, 170, 180, 190) is repeated for each radiological finding type. The detection performed by the object matching engine 160 can be performed, in an embodiment, by computer vision and machine learning technologies, such as by application of the OpenCV libraries. The output of the object matching engine 160 is a list 170 of visual candidates for SOL and other findings with semantic descriptors.

The standard medical vocabularies database 110 is used to generate an expert knowledge database 115. The expert knowledge database 115 uses standard medical vocabularies as a basis. The database 115 is presented as scored relations between (1) diseases and clinical terms and (2) diseases and semantic descriptors. For example, for each type of clinical clue (symptom, past medical history, etc.), the database 115 contains the probability that each clue is related to specific disease, and the probability of specific semantic descriptions, such as shape, density, and margins, of radiological findings are related to a specific disease. This database is created manually by experts. Other similar expert knowledge system can be used in other embodiments.

The reverse inference engine 130 receives entries from the expert knowledge database 115 and the set of clinical terms including the final diagnosis. The reverse inference engine 130 outputs a prioritized list of semantic descriptions for SOL and other findings. In an aspect, the clinical inference engine 130 starts from clinical terms and semantic descriptors of radiological findings to get to a prioritized list of diseases (i.e., differential diagnosis). This reverse clinical inference engine 130 is a clinical inference module that is applied in a reverse manner. That is, the process starts from diagnosis and clinical terms (extracted from clinical documents by the textual analysis engine 120) and produces a list of possible semantic descriptors that can be prioritized by probabilities (140). This method in uses the expert knowledge database 115. For example, a simple cyst (diagnosis) in Ultrasound may have high probabilities for following semantic descriptors of SOL: echogenicity SOL will be "anechoic", the shape will be "oval", and the margins will be "circumscribed".

The prioritized list 140 of semantic descriptions for SOL and other findings and the list 170 of visual candidates for SOL and other finding with semantic descriptors are fed into a matching engine 180. This matching engine 180 determines the best visual candidate for SOL and other findings and outputs the best candidate to a manual verification component 190. In the manual verification component 190, the user is presented with an annotated image. The user can accept or reject the annotated image. The acceptance or rejection of the annotation is fed back into the matching engine 180 and can be used to modify its logic.

Images may be annotated according to embodiments of the present invention during all a portion of a medical procedure. In one embodiment, the image annotation will only occur during an image annotation "session" (e.g. a period of time during which image annotation is performed, and before and after which, image annotation is not performed). An image annotation "session" may be initiated and/or terminated by the operator performing a key stroke, issuing a command (such as a verbal command), performing a gesture with a medical device or hand, pressing a button on the medical device, pressing a foot pedal, pressing a button on the medical device (e.g., a button on an annotation stylus), etc.

Figure 2:
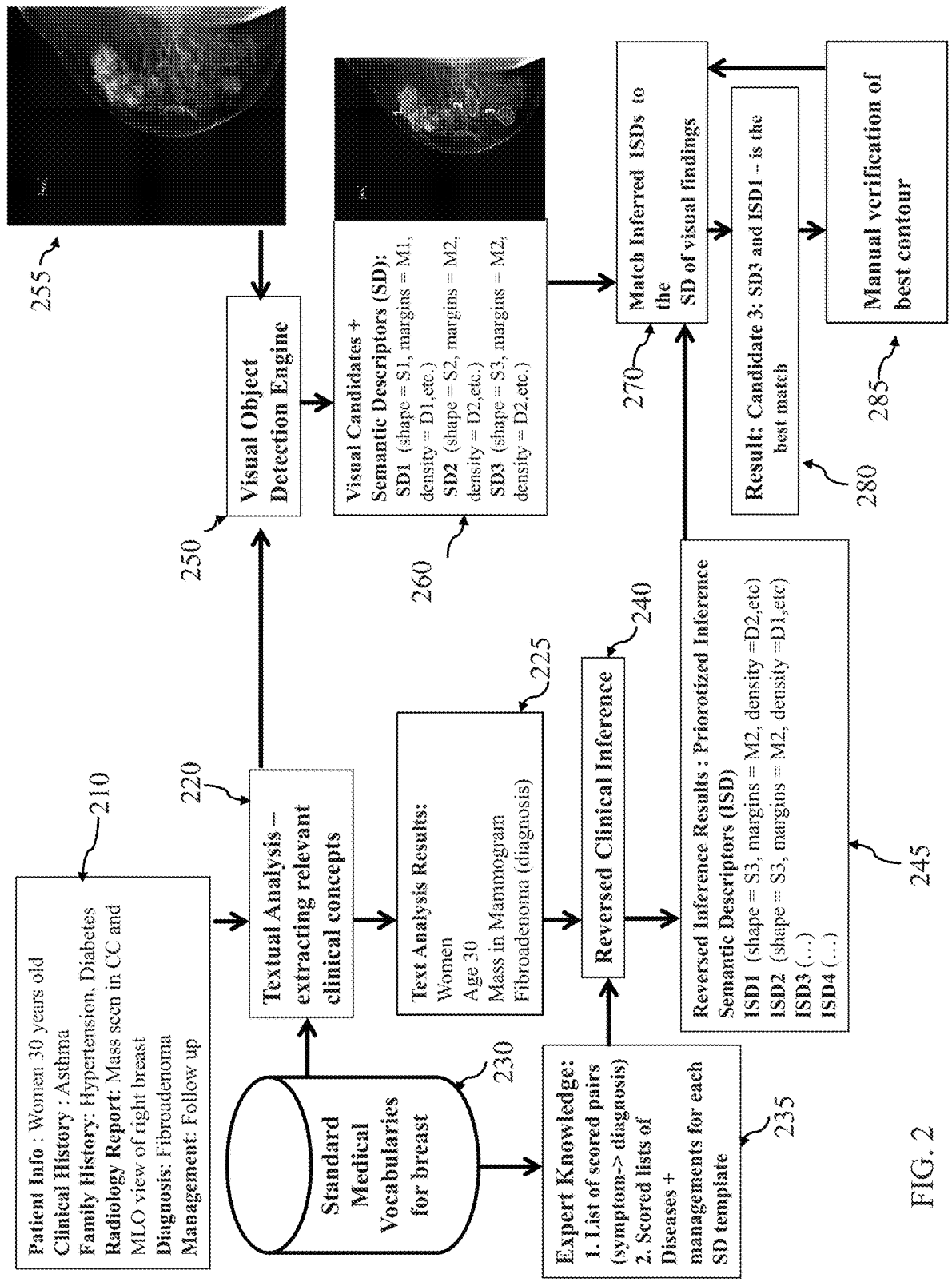
FIG. 2 illustrates an example data flow, according to an embodiment of the present invention.
Figure 3:
FIG. 3 shows an example image data, according to an embodiment of the present invention.
Figure 4:
FIG. 4 shows an example of image data with locations marked, according to an embodiment of the present invention.
Figure 5:
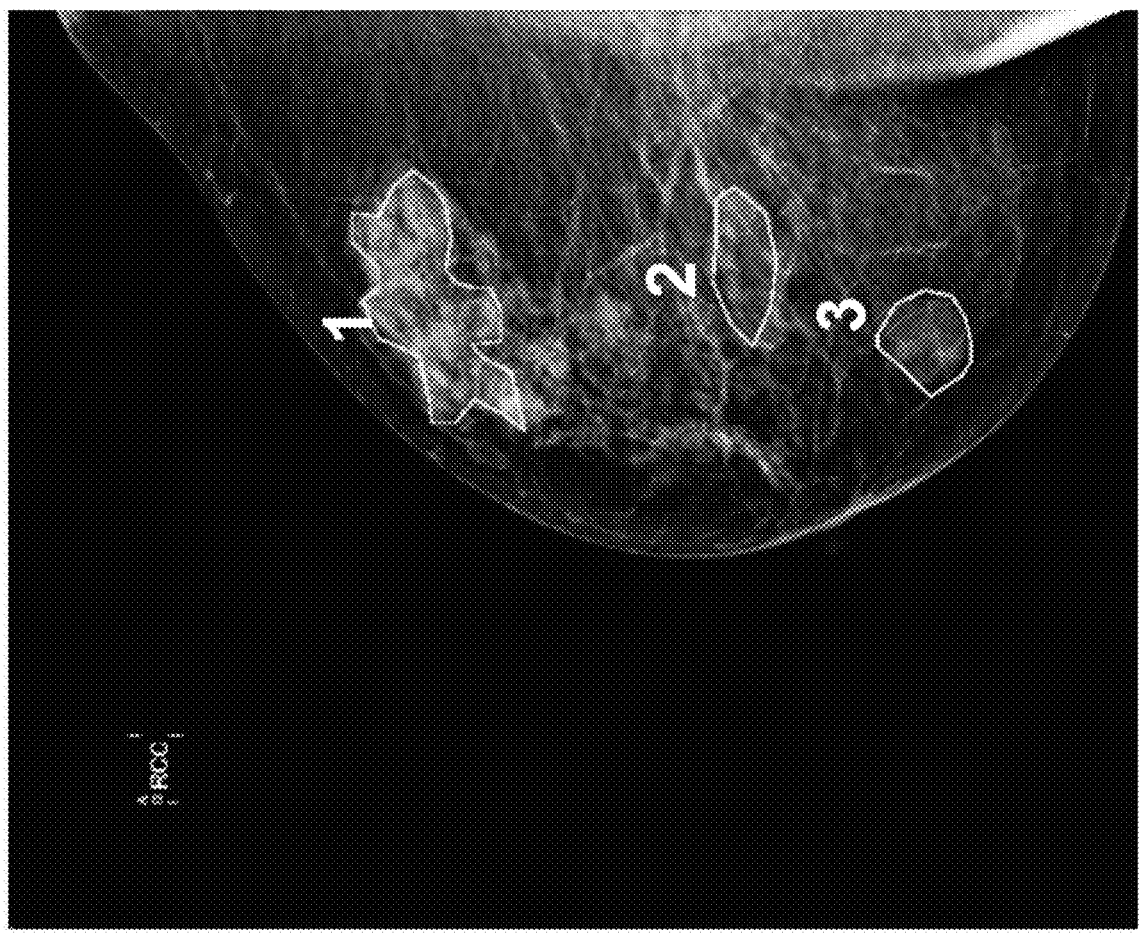
FIG. 5 shows an example of image data with locations marked and labeled, according to an embodiment of the present invention.

FIG. 2 illustrates an example data flow, according to an embodiment of the present invention. In this example, the image data 255 is that of a breast, and is also shown in FIG. 3. The textual data 210 provides textual patient information such the clinical history and family history. The textual analysis engine 220 uses the standard medical vocabularies database 230 to extract the relevant clinical concepts to produce the text analysis results 225. An expert knowledge database 235 is used, along with the text analysis results 225, by the reverse inference engine 240 that produces 245 prioritized list of semantic descriptors The visual object matching engine 250 uses the image data 255 and the output of the textual analysis engine 220 to determine the location and semantic descriptors 260 of all candidates for the radiological finding type extracted by the textual analysis engine 220. An example of the locations can be seen in FIG. 4. The matching engine 270 determines the best candidate for SOL and other findings and outputs the best candidate 280 to a manual verification component 285. An example output of the contours along with the label corresponding to the findings is shown in FIG. 5.

The above-described techniques can be implemented in digital electronic circuitry, or in computer hardware, firmware, software, or in combinations of them. The implementation can be as a computer program product, i.e., a computer program tangibly embodied in an information carrier, e.g., in a machine-readable storage device or in a propagated signal, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps can be performed by one or more programmable processors executing a computer program to perform functions of the invention by operating on input data and generating output. Method steps can also be performed by, and apparatus can be implemented as, special purpose logic circuitry, e.g., an FPGA (field programmable gate array) or an ASIC (application-specific integrated circuit). Modules can refer to portions of the computer program and/or the processor/special circuitry that implements that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer also includes, or is operatively coupled to receive data from or transfer data to, or both, one or more mass storage devices for storing data, e.g., magnetic, magneto-optical disks, or optical disks. Data transmission and instructions can also occur over a communications network. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

To provide for interaction with a user, the above described techniques can be implemented on a computer having a display device for displaying information to the user and a keyboard and a pointing device, e.g., a mouse or a trackball, by which the user can provide input to the computer (e.g., interact with a user interface element). Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The above described techniques can be implemented in a distributed computing system that includes a back-end component, e.g., as a data server, and/or a middleware component, e.g., an application server, and/or a front-end component, e.g., a client computer having a graphical user interface and/or a Web browser through which a user can interact with an example implementation, or any combination of such back-end, middleware, or front-end components. The components of the system can be interconnected by any form or medium of digital data communication, e.g., a communication network. Examples of communication networks include a local area network ("LAN") and a wide area network ("WAN"), e.g., the Internet, and include both wired and wireless networks. The computing system can include clients and servers.

While the foregoing written description of the invention enables one of ordinary skill to make and use what is considered presently to be the best mode thereof, those of ordinary skill will understand and appreciate the existence of alternatives, adaptations, variations, combinations, and equivalents of the specific embodiment, method, and examples herein. Those skilled in the art will appreciate that the within disclosures are exemplary only and that various modifications may be made within the scope of the present invention. In addition, while a particular feature of the teachings may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising."

Other embodiments of the teachings will be apparent to those skilled in the art from consideration of the specification and practice of the teachings disclosed herein. The invention should therefore not be limited by the described embodiment, method, and examples, but by all embodiments and methods within the scope and spirit of the invention. Accordingly, the present invention is not limited to the specific embodiments as illustrated herein, but is only limited by the following claims.

We claim:

1. A method for medical image annotation comprising:
   receiving patient case files from a data interface, each patient case file comprising a set of textual information and a set of image data;
   extracting a set of clinical terms, including a radiological finding type, from the set of textual information by matching the set of textual information with a medical vocabulary database;
   performing a reverse inference on the set of extracted clinical terms by applying a set of expert knowledge to produce a prioritized list of semantic descriptors for the radiological finding type;
   determining, by a visual object matching engine, from an image of the set of image data and the radiological finding type, a location and semantic descriptors of visual candidates for the radiological finding type in the image;
   determining a best match candidate for the radiological finding type for each of the patient case files, by using the prioritized list of semantic descriptors for the radiological finding type and the visual candidates for the radiological finding type; and
   storing the set of image data linked with the prioritized list of semantic descriptors for the best match candidate for the radiological finding type in a storage system to be searchable and viewable by a medical practitioner.

2. The method of claim 1, wherein the set of expert knowledge comprises a scored list of diseases and managements.

3. The method of claim 1, wherein the set of expert knowledge comprises a list of scored pairs of symptom to diagnosis.

4. The method of claim 1, wherein the set of expert knowledge comprises a probability that semantic descriptions are related to a specific disease.

5. The method of claim 1, wherein the set of expert knowledge comprises a probability that a clinical clue is related to a specific disease.

6. The method of claim 1, wherein the set of semantic descriptors comprises a set of shape, density, and margin descriptions.

7. The method of claim 1, wherein performing object detection comprises applying a machine learning algorithm.

* * * * *